United States Patent [19]
Alexander

[11] Patent Number: 5,460,611
[45] Date of Patent: Oct. 24, 1995

[54] SAFETY SYRINGE

[75] Inventor: Gary E. Alexander, Baton Rouge, La.

[73] Assignee: Medisys Technologies, Inc., Baton Rouge, La.

[21] Appl. No.: 301,541

[22] Filed: Sep. 6, 1994

[51] Int. Cl.⁶ ............................................. A61M 5/00
[52] U.S. Cl. ........................... 604/110; 604/192; 604/263
[58] Field of Search ............................. 604/110, 111, 604/187, 192, 198, 263, 218

[56] References Cited

U.S. PATENT DOCUMENTS

| | | | |
|---|---|---|---|
| 4,026,287 | 5/1977 | Haller | 128/215 |
| 4,197,846 | 4/1980 | Bucalo | 128/218 |
| 4,425,120 | 1/1984 | Sampson | 604/198 |
| 4,581,021 | 4/1986 | Landau et al. | 604/212 |
| 4,636,202 | 1/1987 | Lowin et al. | 604/236 |
| 4,702,738 | 10/1987 | Spencer | 604/198 |
| 4,875,895 | 10/1989 | Kurtz | 604/187 |
| 4,883,472 | 11/1989 | Michel | 604/208 |
| 4,894,055 | 1/1990 | Sudnak | 604/198 |
| 4,936,830 | 6/1990 | Verlier | 604/110 |
| 4,944,723 | 7/1990 | Haber et al. | 604/110 |
| 4,966,592 | 10/1990 | Burns et al. | 604/198 |
| 4,973,316 | 11/1990 | Dysarz | 604/195 |
| 4,973,317 | 11/1990 | Bobrove | 604/198 |
| 4,976,701 | 12/1990 | Ejlersen et al. | 604/192 |
| 4,986,819 | 1/1991 | Sobel | 604/198 |
| 5,015,240 | 5/1991 | Soproni et al. | 604/192 |
| 5,026,353 | 6/1991 | Bartman | 604/192 |
| 5,032,117 | 7/1991 | Motta | 604/88 |
| 5,092,851 | 3/1992 | Ragner | 604/192 |
| 5,092,852 | 3/1992 | Poling | 604/192 |
| 5,098,401 | 3/1992 | De Lange | 604/192 |
| 5,104,384 | 4/1992 | Parry | 604/192 |
| 5,122,123 | 6/1992 | Vaillancourt | 604/192 |
| 5,135,507 | 8/1992 | Haber et al. | 604/187 |
| 5,151,088 | 9/1992 | Allison et al. | 604/192 |
| 5,282,792 | 2/1994 | Imbert | 604/187 |
| 5,300,038 | 4/1994 | Haber et al. | 604/187 |
| 5,306,258 | 4/1994 | de la Fuente | 604/198 |
| 5,314,503 | 5/1994 | Bobrove et al. | 604/164 |
| 5,342,320 | 8/1994 | Cameron | 604/198 X |

Primary Examiner—John D. Yasko
Attorney, Agent, or Firm—William D. Kiesel; Robert C. Tucker; Russel O. Primeaux

[57] ABSTRACT

A safety syringe is disclosed. The syringe includes a syringe barrel, a plunger, a needle, a needle sleeve, and a pushrod. At one of the pushrod is attached to the needle sleeve while the other end of the pushrod protrudes slightly into the needle end of the syringe barrel. When the injection is administered to the patient, the plunger travels all the way to the needle end of the syringe barrel. The plunger contacts the pushrod which causes the sleeve to cover the needle point automatically as the injection is given.

7 Claims, 1 Drawing Sheet

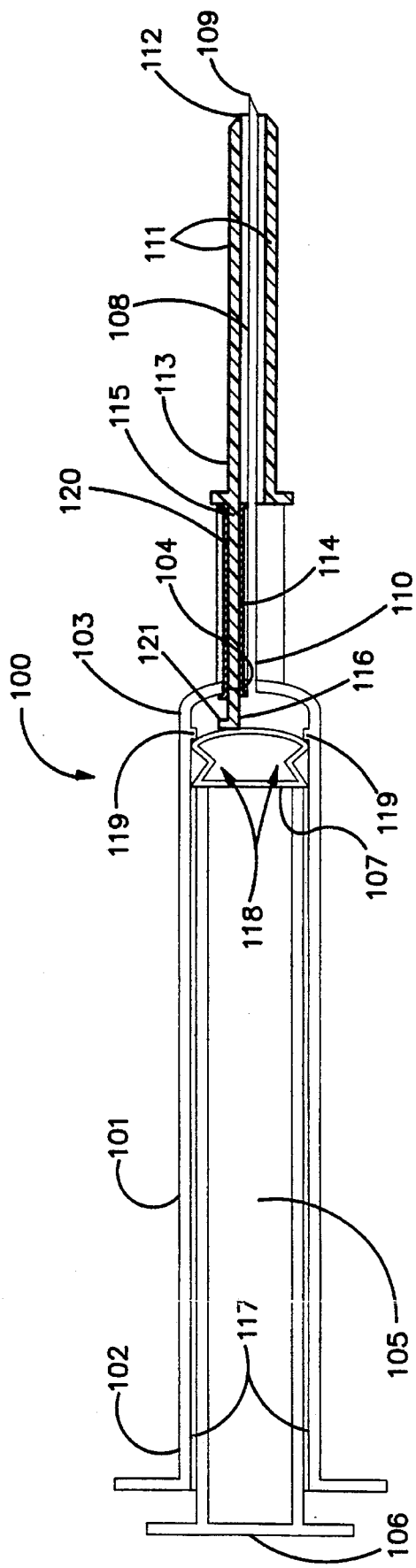
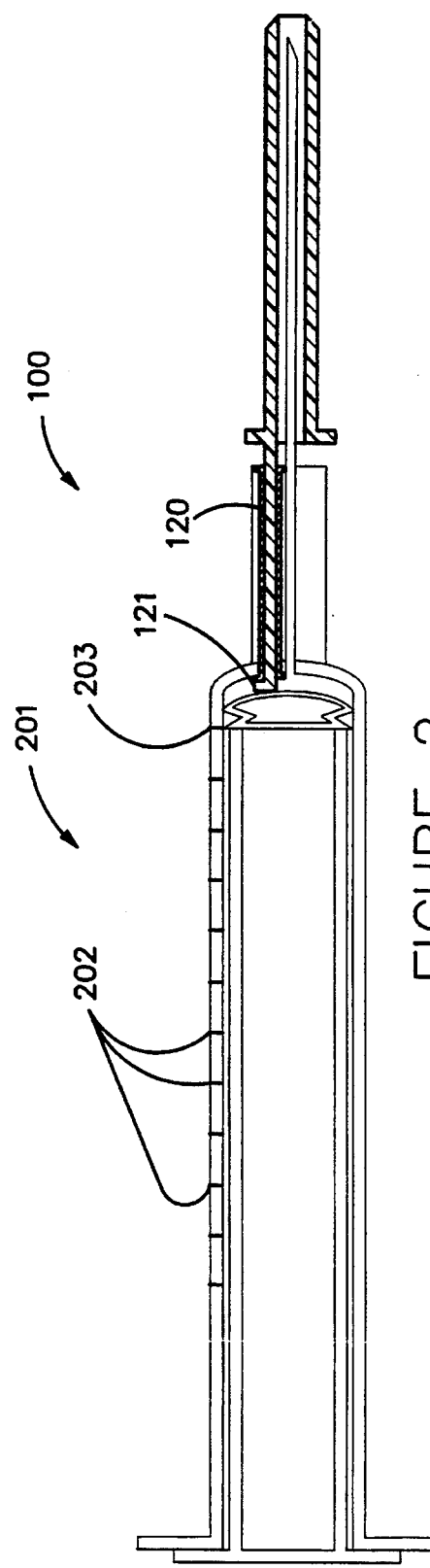
FIGURE 1
FIGURE 2

SAFETY SYRINGE

BACKGROUND OF THE INVENTION

1. Field of the Invention

This invention relates, generally, to syringes, and particularly, syringes designed for shielding the needle of the syringe so as to prevent accidental sticks.

2. Prior Art

In the medical field, prevention of accidental sticks by used needles is a constant concern. Countless injections using syringes are made every day in a variety of settings. As with all medical procedures, prevention of infection is a primary concern. Syringes are typically packaged with a protective cover over the needle. The operator removes this cover prior to administering the injection.

If the syringe has not come pre-filled, the operator will draw up the medication, which is in fluid form, into the syringe. The fluid is drawn into the syringe by inserting the needle into the container of medication fluid. The syringe plunger is pulled away from the needle end of the syringe barrel, creating a vacuum in the syringe. The vacuum causes the medication to be drawn into the syringe through the needle. The operator observes the position of the syringe plunger in relation to volume marks found on the syringe body. When the plunger has reached the desired mark corresponding to the correct dosage, the operator removes the needle from the container and holds the syringe, needle end up, so that all air in the syringe will go to the needle. The operator then pushes in the plunger slightly, sometimes tapping the side of the syringe, until any air in the syringe has been purged out through the needle.

The operator sets the syringe aside and prepares the injection site. Once the injection site is prepared, the operator inserts the needle into the patient and pushes in the plunger, injecting the medication into the patient. When the plunger has been fully depressed into the syringe body, the operator removes the needle from the patient.

The next few moments are crucial in infection control. The used syringe, immediately after it has been removed from the patient, is commonly known as a dirty needle. Frequently, hospitals and physicians' offices have special receptacles in the patient and examining rooms for disposal of dirty needles. The operator will usually replace the cover on the needle and place the syringe into a proper receptacle. But in the few moments, or even the few seconds, between the removal of the syringe from the patient and the placement of the cover over the needle an accidental dirty needle stick can occur.

Dirty needle sticks can occur during this time for any number of reasons. In emergency rooms and other settings, patient may be fighting the treatment, and may push the used needle into the operator or other medical professionals around the patient. Children or even some adults become frightened by the pain of a shot and may react, involuntarily or voluntarily, by jerking or some other motion which can cause an accidental stick. Other factors not attributable to the patient include fatigue of the operator, poor lighting conditions (e.g. at night in a patient's dark room), and simple lapses in following procedures. Some of these conditions may cause the operator to stick themselves when simply replacing the cover on the needle.

Numerous attempts have been made to provide a device which will prevent or minimize dirty needle sticks. U.S. Pat. No. 4,973,316 to Dysarz discloses a syringe in which a compressed spring assembly within the syringe barrel is used in combination with a trigger assembly. The device in Dysarz retracts the needle after the injection is given. However, the device in Dysarz requires the use of numerous moving parts and an internal spring in the syringe body. The device in Dysarz also requires separate manipulation of the syringe by the operator after giving the injection. Dysarz does not disclose automatic shielding of the needle with the administration of the injection.

What is needed is a syringe which will automatically cover the needle upon the administering of the injection. An ideal syringe would cover the needle without the operator having to use a second hand and would cover the needle simultaneously with the giving of the injection. The automatic covering feature should not interfere with the syringe's ability to perform all the functions of a conventional syringe, to include the ability to draw up medications and purge air from the medication.

OBJECTS OF THE INVENTION

It is an object of the present invention to provide a syringe which will automatically cover the needle upon the administering of the injection to the patient.

Another object of the present invention is to provide a syringe which will perform the automatic covering of the needle without the operator having to use a second hand.

Another object of the present invention is to provide a device which is compatible with current medication packaging, specifically, the syringe must be able to draw up medications and purge air from the drawn up medication.

Another object of the present invention is to provide a device which is relatively easy and inexpensive to manufacture and which is simple in operation.

SUMMARY OF THE INVENTION

A safety syringe is disclosed. The syringe includes a syringe barrel, a plunger, a needle, a needle sleeve, and a pushrod. The pushrod is attached to the needle sleeve at one end while the other end protrudes slightly into the needle end of the syringe barrel. When the plunger is fully inserted into the barrel to administer an injection, the plunger moves the pushrod. The pushrod in turn moves the sleeve to a position in which the sleeve covers the needle.

An advantage of the invention is that it automatically covers the pointed end of the needle of the syringe as the operator administers the injection.

A further advantage of the invention is that the operator does not have to use a second hand to cover the needle.

A further advantage of the invention is that the syringe can still be used in the conventional manner for drawing up medications.

A further advantage of the invention is that it is relatively inexpensive and easy to manufacture and is very simplistic in its operation.

These and other objects, features, and advantages of this invention will be apparent from the following descriptions of the invention.

BRIEF DESCRIPTION OF THE DRAWINGS

FIG. 1 is a sectional view of the invention with the sleeve in the exposed position.

FIG. 2 is a sectional view of the invention with the sleeve in the covered position.

DETAILED DESCRIPTION

Referring to FIG. 1, a sectional view of safety syringe 100 is shown with the sleeve in the exposed position. Safety syringe 100 would probably be shipped and packaged with a removable cover (not shown). The principle components of safety syringe 100 are barrel 101, plunger 105, needle 108, sleeve 111, and connector 114.

Barrel 101 is an elongated hollow cylindrical member made of a rigid or semi-rigid material such as molded plastic. Barrel 101 is transparent or translucent so that the operator can see the medication in barrel 101. Barrel 101 has plunger end 102 which is open for receipt of plunger 105 and needle end 103. Needle end 103 is like the needle end on conventional syringes known in the art except it has connector aperture 104. Connector aperture 104 can be of any shape so long as its shape matches with the cross-sectional shape of connector 114 so that when connector 114 is inserted into connector aperture 104 a fluid-tight seal is formed. In the embodiment shown connector aperture 104 is a cylindrical shaped hole whose long axis is parallel with the long axis of barrel 101.

Plunger 105 has thumb end 106 and washer end 107. Plunger 105 is an elongated rigid or semi-rigid member whose length is adapted so that the operator can fully insert plunger 105 into barrel 101 by pushing on thumb end 106. Plunger 105 will typically be constructed of molded plastic. Washer end 107 is adapted so that when washer end 107 is inserted into barrel 101 a fluid-tight seal is formed between washer end 104 and barrel 101. Washer end may be constructed with an optional washer or plurality of washers to form this fluid-tight seal. Or, as depicted, washer end 104 may be constructed with no washers, a configuration in which washer end is sized to correspond with the inner dimensions of barrel 101.

Washer end 107 has a single, continuous, smooth, sealed surface which pushes the medication from barrel 101. Needle 108 is a hollow rigid elongated member typically constructed from a strong metal such as stainless steel. Needle 108 has pointed end 109 which will make the puncture into the patient. Opposite pointed end 109 is syringe end 110 of needle 108 which is rigidly connected to needle end 103 of syringe 101. Syringe end 110 can be affixed to barrel 101 by any conventional method known in the art such as gluing or making syringe end 110 with a tab which is perpendicular to needle 108 and locked into needle end 103 of barrel 101.

Safety syringe 100 includes sleeve 111 which is an elongated hollow semi-rigid member slidably positionable over needle 108. Sleeve 111 has a point-covering end 112 and connecting end 113. Sleeve 111 can be moved along needle 108 between two positions—an exposed position depicted in FIG. 1 in which sleeve 111 covers substantially all of needle 108 except a small portion of needle 108 at pointed end 109, and a safe position depicted in FIG. 2 in which sleeve 111 covers substantially all of needle 108 including pointed end 109. Sleeve 111 is sufficiently thin and is immediately adjacent to needle 108 so that sleeve 111 will go into the tissue of the patient and cover needle 108 as sleeve 111 moves into the safe position.

Passing through connector aperture 104 is connector 114. Connector 114 is an elongated rigid or semi-rigid member having sleeve end 115 and barrel end 116. Barrel end 116 is adapted to have the same cross-sectional shape as connector aperture 104 so that barrel end 115 is slidably inserted through connector aperture 104.

When sleeve 111 is in the exposed position barrel end 115 protrudes into barrel 101 a pre-determined distance. In the embodiment depicted, this pre-determined distance is approximately one-fourth of an inch. However, one skilled in the art could practice the invention with this distance being greater and lesser than one-fourth of an inch. Sleeve end 115 of connector 114 is connected to sleeve 111 so that as plunger 105 is depressed into barrel 101, washer end 107 will contact connector 114 which will cause sleeve 111 to move to the safe position. In the embodiment depicted, connector 114 and sleeve 111 form a unitary member, but one skilled in the art could practice the invention with sleeve 111 and connector 114 being separate members.

Although in the embodiment depicted, sleeve 111 is made of Teflon and connector 114 is made of molded plastic, one could use any semi-rigid material for sleeve 111 and any rigid or semi-rigid material for connector 114. Additionally, although the embodiment depicted shows only one connector 114, one could practice the invention with two or more connectors.

Connector 114 and connector aperture 104 are adapted such that they form a fluid-tight seal while still allowing connector 114 to be slidable within and through connector aperture 104. In the embodiment depicted this fluid tight seal is achieved by using grommet 120 which will fit between connector 114 and connector aperture 104. One skilled in the art could also practice the invention without grommet 120. Without grommet 120 the fluid-tight seal would be achieved by appropriately sizing connector 114 and connector aperture 104.

Connector 114 includes catch 121 at barrel end 116. Catch 121 prevents connector 114 and sleeve 111 from being pulled out of barrel 101 when safety syringe 100 is removed from the patient. In the embodiment depicted catch 121 is a small tab integral to connector 114 but one skilled in the art could practice the invention with catch 121 being a lip completely surrounding connector 114 or using any conventional means to prevent connector 114 from passing completely out of connector aperture 104.

In order to allow medication to be drawn into safety syringe 101 while still preserving the automatic needle-covering feature of safety syringe 100, one or more stop means 118 are fixably attached to interior wall 117 of barrel 101. Stop means 118 are positioned intermediate needle end 103 and plunger end 102 of barrel 101. Stop means 118 are adapted so that stop means 118 engage washer end 107 so as to prevent plunger 105 from traveling past stop means 118 and moving connector 114. Stop means are also adapted such that if the operator applies sufficient force washer 107 can travel beyond stop means 118 and move connector 114 which in turn moves sleeve 111 from the exposed position to the safe position.

In the embodiment depicted stop means 118 are one or more nibs 119. Nibs 119 are deformable plastic members which protrude from interior wall 117 a sufficient distance so as to engage washer end 107. Upon the application of sufficient force by the operator on thumb end 106 of plunger 105, nibs 119 deform and bend, thereby allowing washer end 107 to travel all the way to needle end 103 of barrel 101, causing sleeve 101 to move to the safe position.

Although in the embodiment depicted, stop means 118 are nibs 119, one skilled in the art could make stop means 118 by making barrel 101 of smaller diameter at needle end 103 and making washer end 107 with deformable members two diameters. Stop means 118 could also be a sliding tab, perpendicular to the long axis of barrel 101, the tab being adapted such that the operator could push it into or pull it out of the barrel, or any other conventional means of selectively stopping the travel of a syringe plunger in a syringe barrel.

Stop means 118 is positioned a sufficient distance away from needle end 103 of barrel 101 so as to allow connector 114 to protrude into barrel 101 without being moved by washer end 107. Because of this spacing, there will be some air already in safety syringe 100 when fluid is drawn into safety syringe 100. The operator must then purge the air from safety syringe 100 using the conventional method of holding safety syringe vertically with needle 108 pointing upward and depressing plunger 105 into barrel 101 until the air is expelled from needle 108. Stop means 119 cannot be positioned so far back from needle end 103 of barrel 101 that an inordinate amount of air will be disposed in safety syringe 100 after drawing medication. The air must be able to be expelled by moving plunger 105 toward said plunger end 102 of barrel 101 without moving washer end 107 beyond stop means 118.

In most conventional syringes known in the art, there are marks on the syringe barrel to indicate volume measurements of fluid in the syringe. Safety syringe 100 will have volume marks 201 along barrel 101 which will indicate the amount of fluid which has been drawn into barrel 101. Volume marks 201 will include zero mark 203 and at least one unit mark 202. The zero mark will be aligned with stop means 118. In the embodiment depicted one could eliminate zero mark 203 and use nibs 119 as zero mark 203. Zero mark 203 and unit marks 202 can be make by lines painted or etched on barrel 101.

Safety syringe 100 is shipped in sterile packaging and normally will have a removable cover (not shown) over needle 108 and sleeve 111. In operation, the operator removes the removable cover and inserts needle 108 into a container of medication fluid. The operator pulls plunger 105 in a direction away from needle 108 so that the fluid is drawn into barrel 101 until washer end 107 is in alignment with the appropriate unit marks 202. The operator withdraws needle 108 from the container. The operator pushes the needle into the injection site on the patient. Once the needle is appropriately positioned in the patient, the operator pushes on thumb end 106 of plunger 105, applying enough force to move washer end 107 of plunger 105 past stop means 118 to needle end 103 of barrel 101. This movement causes sleeve 111 to move from the exposed position to the safe position while pointed end 109 of needle 108 is still in the patient. The operator removes safety syringe 100 from the patient and disposes of safety syringe 100. The operation for covering pointed end 109 of needle 108 is thus automatic with the administration of the injection and is a one-handed operation.

There are of course other alternate embodiments which are obvious from the foregoing descriptions of the invention which are intended to be included within the scope of the invention as defined by the following claims:

I claim:

1. A safety syringe for administering an injection into tissue, said safety syringe comprising:

a barrel having a plunger end and a needle end, said needle end having a single connector aperture;

a plunger having a thumb end and a washer end, said plunger and said washer end being adapted such that said washer end of said plunger may be inserted into said plunger end of said barrel and form a fluid-tight seal between said washer end and said barrel, said washer end having a single, continuous, smooth, sealed washer surface for pushing medication out of said barrel:

a hollow needle, pointed at only one end, said needle having a pointed end and a syringe end, said syringe end of said needle being rigidly connected to said needle end of said syringe;

a sleeve slidably positionable over said needle, said sleeve having a point-covering end and a connecting end, said sleeve being movable from an exposed position to a safe position, said exposed position being a position wherein said sleeve covers substantially all of said needle leaving only a small portion of said needle at said pointed end exposed, said safe position being a position wherein said sleeve covers substantially all of said needle including said pointed end, said sleeve being further adapted such that said sleeve is immediately adjacent to said needle and will move into said safe position while said needle is still in said tissue;

a single connector, said single connector being an elongated rod having a sleeve end and a barrel end, said sleeve end of said connector being operably connected to said connecting end of said sleeve, said barrel end of said connector being slidably insertable through said connector aperture, said connector and said connector aperture being adapted such that a portion of said barrel end of said connector protrudes into said barrel, said connector and said sleeve being adapted such that as said washer end of said plunger travels to said needle end of said barrel, said connector will move said sleeve from said exposed position to said safe position.

2. The apparatus in claim 1, wherein said connector further comprises a catch at said barrel end of said connector, said catch being adapted such that said catch will engage said needle end of said barrel as said plunger travels to said needle end of said barrel.

3. The apparatus in claim 2, wherein said single connector and said sleeve are joined as one unitary member.

4. The apparatus in claim 3, further comprising:

an interior wall of said barrel; and one or more stop means attached to said interior wall near said needle end of said barrel and intermediate said needle end and said plunger end of said barrel, said stop means being adapted for engaging and stopping the travel of said washer end toward said needle end of said barrel, said stop means being further adapted such that said washer end may be moved past said stop means upon the application of sufficient force to said plunger by the operator.

5. The apparatus in claim 4, wherein said stop means are positioned such that an operator may draw fluid into said barrel by moving said plunger toward said plunger end of said barrel and purge air from said fluid by pushing said plunger toward said needle end of said barrel without moving said washer end of said plunger beyond said stop means.

6. The apparatus in claim 5, wherein said barrel further comprises volume marks for indicating the amount of fluid which has been drawn into said barrel, said volume marks including a zero mark and at least one unit mark, said zero mark being aligned with said stop means.

7. A method of administering an injection into the tissue of a patient comprising:

(1) preparing a safety syringe for use, said safety syringe comprising:

(i) a barrel having a plunger end, an interior wall, and a needle end, said needle end having a single connector aperture;

(ii) a plunger having a thumb end and a washer end, said plunger and said washer end adapted such that said washer end of said plunger may be inserted into said plunger end of said barrel and form a fluid-tight seal between said washer end and said barrel, said washer end having a single, continuous, smooth, sealed washer surface for pushing medication out of said barrel;

(iii) a hollow needle, pointed at only one end, said needle having a pointed end and a syringe end, said syringe end of said needle being rigidly connected to said needle end of said syringe;

(iv) a sleeve slidably positionable over said needle, said sleeve having a point-covering end and a connecting end, said sleeve being movable from an exposed position to a safe position, said exposed position being a position wherein said sleeve covers substantially all of said needle leaving only a small portion of said needle at said pointed end exposed, said safe position being a position wherein said sleeve covers substantially all of said needle including said pointed end, said sleeve being further adapted such that said sleeve is immediately adjacent to said needle and will move into said safe position while said needle is still in said tissue;

(v) a single connector, said single connector being an elongated rod having a sleeve end and a barrel end, said sleeve end of said connector being operably connected to said connecting end of said sleeve, said barrel end of said connector being slidably insertable through said connector aperture, said connector and said connector aperture being adapted such that a portion of said barrel end of said connector protrudes into said barrel, said connector and said sleeve being adapted such that as said washer end of said plunger travels toward said needle end of said barrel, said connector will move said sleeve from said exposed position to said safe position; and (vi) one or more stop means attached to said interior wall near said needle end of said barrel and intermediate said needle end and said plunger end, said stop means being adapted such that said stop means engages and stops the travel of said washer end toward said needle end of said barrel, said stop means being further adapted such that said washer end may travel past said stop means upon the application of sufficient force by the operator.

(2) inserting said pointed end of said needle into a container of medication fluid and drawing up a desired amount of said fluid;

(3) withdrawing said needle from said container;

(4) inserting said pointed end of said needle into said patient;

(5) pushing on said thumb end of said plunger with enough force to cause said washer end of said plunger to travel past said stop means;

(6) continuing to push on said thumb end so as to cause said sleeve to move from said exposed position to said safe position; and (7) removing said safety syringe from said patient.

* * * * *